United States Patent
Kubo et al.

(10) Patent No.: US 12,295,544 B2
(45) Date of Patent: May 13, 2025

(54) ENDOSCOPE SYSTEM AND IMAGE PROCESSING METHOD

(71) Applicant: OLYMPUS CORPORATION, Tokyo (JP)

(72) Inventors: Kei Kubo, Hino (JP); Makoto Igarashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 18/213,043

(22) Filed: Jun. 22, 2023

(65) Prior Publication Data

US 2023/0329522 A1   Oct. 19, 2023

Related U.S. Application Data (63) Continuation of application No. 17/009,055, filed on Sep. 1, 2020, now Pat. No. 11,723,513, which is a (Continued)

(30) Foreign Application Priority Data

Mar. 5, 2018   (JP) ................................. 2018-038794

(51) Int. Cl.
A61B 1/00   (2006.01)
A61B 1/04   (2006.01)
A61B 1/06   (2006.01)

(52) U.S. Cl.
CPC .... *A61B 1/000094* (2022.02); *A61B 1/00045* (2013.01); *A61B 1/044* (2022.02); *A61B 1/046* (2022.02); *A61B 1/0638* (2013.01)

(58) Field of Classification Search
None
See application file for complete search history.

(56) References Cited

U.S. PATENT DOCUMENTS 4,553,079 A * 11/1985 Igarashi ................ B31B 50/006
                                                      318/626
7,204,803 B2 * 4/2007 Ueno ................... A61B 1/0655
                                                      600/921
(Continued)

FOREIGN PATENT DOCUMENTS

EP   2 719 317 A1   4/2014
JP   06-66808 A     3/1994
(Continued)

OTHER PUBLICATIONS

US Office Action dated Oct. 13, 2022 received in U.S. Appl. No. 17/009,055.
(Continued)

*Primary Examiner* — John P Leubecker
*Assistant Examiner* — Jae Woo
(74) *Attorney, Agent, or Firm* — Scully, Scott, Murphy & Presser, P.C.

(57) ABSTRACT

An endoscope system includes a light source apparatus to generate an illumination light including a first light in a red to near infrared region, a second light in a green region, and a third light in a blue region, an image pickup device to pick up an image of an object and output an image pickup signal, and a processor to generate a first to third color components corresponding to the first to third lights based on an image generated according to the image pickup signal. The processor generates two of three color components that are blue, green, and red included in an observation image by using a second color component, and generates one remaining color component by using a first color component, and generates respective color components of red, green, and blue included in a white light observation image by using the first to third color components.

15 Claims, 4 Drawing Sheets

Related U.S. Application Data continuation of application No. PCT/JP2018/046340, filed on Dec. 17, 2018.

(56) References Cited

U.S. PATENT DOCUMENTS

| | | | |
|---|---|---|---|
| 8,517,929 B2* | 8/2013 | Kuroda | A61B 1/05 600/109 |
| 9,095,250 B2* | 8/2015 | Yamaguchi | A61B 1/0638 |
| 9,949,624 B2 | 4/2018 | Igarashi | |
| 10,709,310 B2 | 7/2020 | Aoyama | |
| 11,723,513 B2* | 8/2023 | Kubo | A61B 1/000094 600/160 |
| 12,029,385 B2* | 7/2024 | Makino | A61B 1/000094 |
| 2004/0037454 A1 | 2/2004 | Ozawa et al. | |
| 2007/0153542 A1* | 7/2007 | Gono | A61B 1/063 362/574 |
| 2008/0249368 A1* | 10/2008 | Takei | A61B 1/0655 600/181 |
| 2009/0023991 A1* | 1/2009 | Gono | G01J 3/32 600/109 |
| 2009/0040298 A1 | 2/2009 | Yamazaki et al. | |
| 2009/0058999 A1* | 3/2009 | Gono | A61B 1/00186 348/71 |
| 2010/0063352 A1* | 3/2010 | Matsuura | H04N 23/68 600/109 |
| 2010/0076304 A1* | 3/2010 | Teramura | A61B 3/1225 250/492.1 |
| 2011/0237883 A1 | 9/2011 | Chun | |
| 2012/0101348 A1* | 4/2012 | Yamaguchi | A61B 1/043 600/109 |
| 2012/0257029 A1* | 10/2012 | Igarashi | A61B 1/044 348/E9.002 |
| 2013/0006109 A1* | 1/2013 | Takei | A61B 1/0646 600/432 |
| 2013/0172675 A1 | 7/2013 | Yamazaki et al. | |
| 2013/0289373 A1* | 10/2013 | Yamamoto | A61B 5/1459 600/339 |
| 2013/0293693 A1* | 11/2013 | Igarashi | G06T 5/92 348/70 |
| 2013/0324797 A1 | 12/2013 | Igarashi et al. | |
| 2013/0329027 A1* | 12/2013 | Igarashi | A61B 1/0638 348/68 |
| 2016/0089010 A1* | 3/2016 | Aoyama | A61B 1/0005 348/70 |
| 2017/0049327 A1 | 2/2017 | Alfano et al. | |
| 2018/0000335 A1 | 1/2018 | Igarashi et al. | |
| 2018/0344136 A1* | 12/2018 | Kikuchi | G02B 23/2484 |
| 2020/0260940 A1* | 8/2020 | Kutsuma | A61B 1/0655 |
| 2020/0397278 A1* | 12/2020 | Kubo | G02B 23/26 |

FOREIGN PATENT DOCUMENTS

| | | |
|---|---|---|
| JP | 2010-069063 A | 4/2010 |
| JP | 5427318 B1 | 2/2014 |
| WO | 2013/145407 A1 | 10/2013 |
| WO | 2016/147436 A1 | 9/2016 |

OTHER PUBLICATIONS

International Search Report dated Mar. 19, 2019 received in PCT/JP2018/046340.

* cited by examiner

ENDOSCOPE SYSTEM AND IMAGE PROCESSING METHOD

CROSS REFERENCE TO RELATED APPLICATIONS

This application is a continuation of U.S. patent application Ser. No. 17/009,055, filed on Sep. 1, 2020, which is a continuation of PCT International Application No. PCT/JP2018/046340, filed on Dec. 17, 2018, which claims priority to Japanese Patent Application No. 2018-038794, filed in Japan on Mar. 5, 2018, the entire contents of each of which are incorporated herein by this reference.

BACKGROUND I/F THE INVENTION

1. Field of the Invention

The present invention relates to an endoscope system and an image processing method, and particularly relates to an endoscope system and an image processing method that are used in observation of living tissue.

2. Description of the Related Art

In endoscope observation in a medical field, there has been conventionally proposed an observation method that visualizes blood vessels existing at a desired depth of living tissue by irradiating the living tissue with a narrow-band light in which a center wavelength (wavelength band) is set according to light absorption characteristics of a biological substance such as hemoglobin.

More specifically, for example, Japanese Patent No. 5427318 discloses a configuration in which a thick blood vessel existing in a deep part of a living mucous membrane is displayed in high contrast by irradiating the living mucous membrane with a narrow-band light in a vicinity of 600 nm that is a light relatively easily absorbed by hemoglobin, and a narrow-band light in a vicinity of 630 nm that is a light relatively hardly absorbed by hemoglobin.

SUMMARY I/F THE INVENTION

An endoscope system of one aspect of the present invention includes a light source apparatus configured to generate a light including a first light having a center wavelength within a wavelength range from a red region to a near infrared region, a second light having a center wavelength in a green region, and a third light having a center wavelength in a blue region, as an illumination light, an image pickup device configured to pick up an image of an object irradiated with the illumination light and output an image pickup signal, and a processor configured to generate a first color component corresponding to the first light, a second color component corresponding to the second light, and a third color component corresponding to the third light respectively, based on an image generated according to the image pickup signal outputted from the image pickup device, wherein the processor generates two color components of three color components that are a blue component, a green component, and a red component included in an observation image that is displayed on a display apparatus at a time of observation of the object by using the second color component and generates one remaining color component of the three color components included in the observation image by using the first color component, and generates a red component included in a white light observation image that is displayed on the display apparatus by using the first color component, generates a green component included in the white light observation image by using the second color component and generates a blue component included in the white light observation image by using the third color component.

An image processing method of one aspect of the present invention includes causing a light source apparatus to generate a light including a first light having a center wavelength within a wavelength range from a red region to a near infrared region, a second light having a center wavelength in a green region, and a third light having a center wavelength in a blue region, as an illumination light, picking up an image of an object irradiated with the illumination light and outputting an image pickup signal, generating a first color component corresponding to the first light, a second color component corresponding to the second light, and a third color component corresponding to the third light respectively, based on an image generated according to the image pickup signal that is outputted, generating two color components of three color components that are a blue component, a green component, and a red component included in an observation image that is displayed on a display apparatus at a time of observation of the object by using the second color component and generating one remaining color component of the three color components included in the observation image by using the first color component, and generating a red component included in a white light observation image that is displayed on the display apparatus by using the first color component, generating a green component included in the white light observation image by using the second color component and generating a blue component included in the white light observation image by using the third color component.

DETAILED DESCRIPTION I/F THE PREFERRED EMBODIMENT

Hereinafter, an embodiment of the present invention will be described with reference to the drawings.

FIG. 1 to FIG. 6 relate to the embodiment of the present invention.

Figure 1:
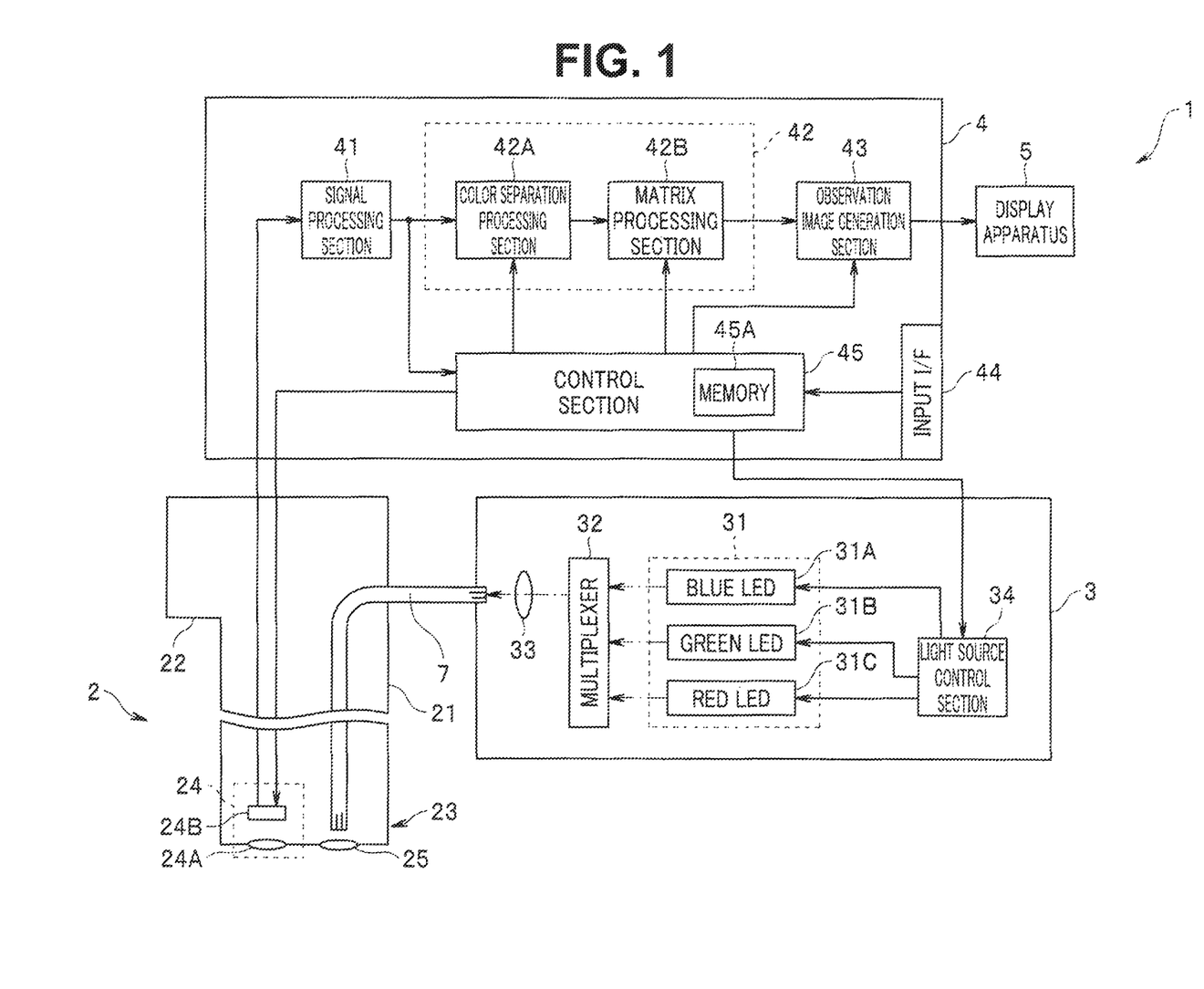
FIG. 1 is a diagram illustrating a configuration of a main part of an endoscope system according to an embodiment.

As illustrated in FIG. 1, an endoscope system 1 has an endoscope 2 that is insertable into a subject and is configured to pick up an image of an object such as living tissue existing in the subject and output an image pickup signal, a light source apparatus 3 configured to supply illumination light that is used in observation of the object via a lightguide 7 inserted and disposed in the endoscope 2, a processor 4 configured to generate an observation image corresponding to the image pickup signal outputted from the endoscope 2 and output the observation image, and a display apparatus 5 configured to display the observation image outputted from the processor 4 on a screen. FIG. 1 is a diagram illustrating a configuration of a main part of the endoscope system according to the embodiment.

The endoscope 2 includes an insertion portion 21 having flexibility and formed into an elongated shape insertable into a subject, and an operation portion 22 provided at a proximal end side of the insertion portion 21. The endoscope 2 is configured to be attachably and detachably connected to the processor 4 via a universal cable (not illustrated) in which a signal line that is used for transmission of various signals such as an image pickup signal outputted from an image pickup section 24 (described later), for example. The endoscope 2 is configured to be connected to the light source apparatus 3 attachably and detachably via a light guide cable (not illustrated) in which at least a part of the lightguide 7 is contained.

In a distal end portion 23 of the insertion portion 21, the image pickup section 24 for picking up an image of an object such as living tissue in a subject, an emission end portion of the lightguide 7, and an illumination optical system 25 that irradiates an object with an illumination light transmitted by the lightguide 7 are provided.

The image pickup section 24 is configured to pick up an image of a return light from an object irradiated with the illumination light from the illumination optical system 25 and output an image pickup signal. More specifically, the image pickup section 24 has an objective optical system 24A configured to form an image of a return light emitted from an object irradiated with the illumination light from the illumination optical system 25, and an image pickup device 24B configured by placing a plurality of pixels for receiving the return light and picking up an image of the return light in a matrix shape according to an image forming position of the objective optical system 24A.

The image pickup device 24B is configured by, for example, an image sensor such as a color CMOS. The image pickup device 24B is configured to perform an image pickup operation corresponding to a control signal outputted from the processor 4. The image pickup device 24B includes a function as an image pickup section, and is configured to generate an image pickup signal by picking up an image of a return light the image of which is formed by the objective optical system 24A, and output the generated image pickup signal to the processor 4.

The operation portion 22 is configured by including such a shape that a user can operate the operation portion 22 by grasping the operation portion 22. The operation portion 22 is provided with a scope switch (not illustrated) configured by including one or more switches capable of making an instruction corresponding to an input operation of the user to the processor 4.

The light source apparatus 3 includes a function as a light source section, and is configured to generate an illumination light for illuminating a surface of an object covered with a liquid at least a part of which includes a bile pigment. The light source apparatus 3 is configured by having a light emitting section 31, a multiplexer 32, a condenser lens 33, and a light source control section 34.

Figure 2:
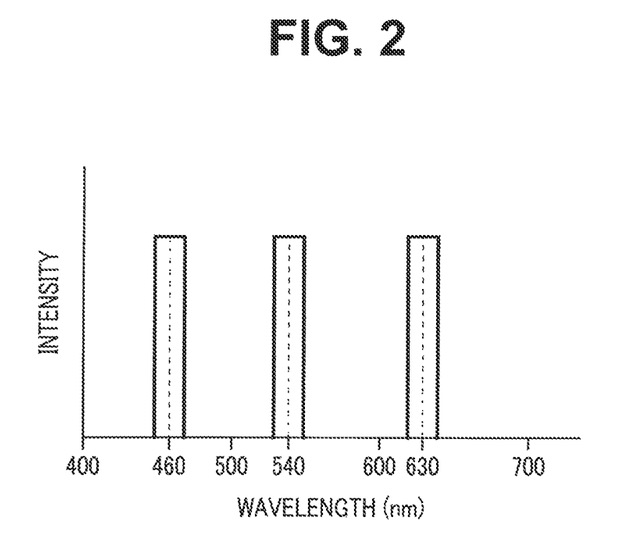
FIG. 2 is a diagram illustrating an example of wavelength bands of lights that are emitted from respective LEDs provided in a light source apparatus of the endoscope system according to the embodiment.

A blue LED 31A is configured to emit a B light that is a blue light (narrow-band) having a center wavelength and intensity in a blue region. More specifically, the blue LED 31A is configured to emit the B light with the center wavelength set to a vicinity of 460 nm, and a bandwidth set to approximately 20 nm, as illustrated in FIG. 2, for example. The blue LED 31A is configured to emit or quench light depending on an LED driving signal that is supplied from the light source control section 34. The blue LED 31A is configured to emit the B light including an amount of emission light corresponding to the LED driving signal that is supplied from the light source control section 34. FIG. 2 is a diagram illustrating examples of wavelength bands of lights that are emitted from respective LEDs provided in the light source apparatus of the endoscope system according to the embodiment.

A green LED 31B is configured to emit a G light that is a green light (narrow-band) having a center wavelength and intensity in a green region. More specifically, the green LED 31B is configured to emit the G light with a center wavelength set to a vicinity of 540 nm, and a bandwidth set to approximately 20 nm, as illustrated in FIG. 2, for example. The green LED 31B is configured to emit or quench light depending on an LED driving signal that is supplied from the light source control section 34. The green LED 31B is configured to emit a G light including an amount of emission light corresponding to the LED driving signal that is supplied from the light source control section 34.

A red LED 31C is configured to emit an R light that is a red light (narrow-band) having a center wavelength and intensity in a red region. More specifically, the red LED 31C is configured to emit the R light with the center wavelength set to a vicinity of 630 nm, and a bandwidth set to approximately 20 nm, as illustrated in FIG. 2, for example. The red LED 31C is configured to emit or quench light depending on an LED driving signal that is supplied from the light source control section 34. The red LED 31C is configured to emit the R light including an amount of emission light corresponding to the LED driving signal that is supplied from the light source control section 34.

The multiplexer 32 is configured to be able to multiplex the respective lights emitted from the light emitting section 31 and cause the respective lights to be incident on the condenser lens 33.

The condenser lens 33 is configured to condense lights incident through the multiplexer 32 and emit the lights to the lightguide 7.

The light source control section 34 is configured by including a control circuit, for example. The light source control section 34 is configured to generate LED driving signals for driving the respective LEDs of the light emitting section 31 and output the LED driving signals, in response to a control signal that is outputted from the processor 4.

The processor 4 is configured by having a signal processing section 41, an image processing section 42, an observation image generation section 43, an input I/F (interface) 44, and a control section 45.

The signal processing section 41 is configured by including a signal processing circuit, for example. The signal processing section 41 is configured to generate image data by applying predetermined signal processing such as A/D conversion to an image pickup signal outputted from the endoscope 2, and output the generated image data to the image processing section 42 and the control section 45 respectively.

The image processing section 42 is configured by having a color separation processing section 42A, and a matrix processing section 42B.

The image processing section 42 is configured by having a color separation processing section 42A, and a matrix processing section 42B.

The color separation processing section 42A is configured to perform color separation processing for generating a plurality of spectral image data respectively corresponding to a plurality of color components included in the image data by using the image data outputted from the signal processing section 41, in response to a control signal outputted from the control section 45. The color separation processing section 42A is configured to output to the matrix processing section 42B the plurality of spectral image data obtained as a processing result of the aforementioned color separation processing.

The matrix processing section 42B is configured to perform matrix processing for generating image data corresponding to the plurality of color components by using the plurality of spectral image data outputted from the color separation processing section 42A, in response to the control signal outputted from the control section 45. The matrix processing section 42B is configured to output to the observation image generation section 43 the image data corresponding to the plurality of color components obtained as a processing result of the aforementioned matrix processing.

The observation image generation section 43 is configured to generate an observation image by selectively allocating the image data corresponding to the plurality of color components outputted from the matrix processing section 42B to a B (blue) channel, a G (green) channel and an R (red) channel of the display apparatus 5, in response to the control signal outputted from the control section 45. The observation image generation section 43 is configured to output the observation image generated as described above to the display apparatus 5.

The input I/F 44 is configured by including one or more switches and/or buttons capable of making an instruction or the like corresponding to an operation of the user. More specifically, the input I/F 44 is configured by including an observation mode change-over switch (not illustrated) capable of making an instruction to set (switch) the observation mode of the endoscope system 1 to either a white light observation mode or a special light observation mode, in response to an operation of the user, for example. Note that in the present embodiment, a switch having a similar function to a function of the aforementioned observation mode change-over switch may be included in a scope switch of the operation portion 22, for example.

The control section 45 is configured by having a memory 45A in which control information and the like that are used at a time of performing control of the respective sections of the endoscope system 1 are stored. The control section 45 is configured to generate a control signal for causing an operation corresponding to the observation mode of the endoscope system 1 to be performed and output the control signal, based on the instruction that is made in the observation mode change-over switch of the input I/F 44. The control section 45 is configured to generate a control signal for setting an exposure time period, a read time period and the like of the image pickup device 24B and output the control signal. The control section 45 is configured to generate a control signal for controlling operations of the respective LEDs of the light emitting section 31 via the light source control section 34 and output the control signal.

The control section 45 is configured to perform brightness detection processing for detecting present brightness in the observation mode set in the input I/F 44, based on the image data outputted from the signal processing section 41. The control section 45 is configured to generate a control signal for causing such a light-adjusting operation to be performed, which brings the present brightness obtained as a processing result of the aforementioned brightness detection processing close to a brightness target value that is set to each observation mode, and output the control signal to the light source control section 34.

Note that in the present embodiment, the respective sections other than the input I/F 44 in the processor 4 may be configured as individual electronic circuits, or may be configured as circuit blocks in an integrated circuit such as FPGA (Field Programmable Gate Array). In the present embodiment, for example, the processor 4 may be configured by including one or more CPUs. By properly modifying the configuration according to the present embodiment, for example, a program for causing the functions of the respective sections other than the input I/F 44 in the processor 4 to be performed may be read from the memory 45A, and an operation corresponding to the read program may be performed in a computer.

The display apparatus 5 includes, for example, an LCD (liquid crystal display), and is configured to be able to display an observation image or the like outputted from the processor 4.

Subsequently, an operation of the present embodiment will be described hereinafter.

After a user such as a surgeon connects the respective sections of the endoscope system 1 and turns on a power supply, the user makes an instruction to set the observation mode of the endoscope system 1 to the white light observation mode by operating the observation mode change-over switch of the input I/F 44.

The control section 45 generates a control signal for causing the B light, the G light and the R light to be simultaneously emitted from the light source apparatus 3 and outputs the control signal to the light source control section 34, when detecting that an instruction to set the observation mode of the endoscope system 1 to the white light observation mode is made. The control section 45 generates a control signal for causing an operation corresponding to the white light observation mode to be performed and output the control signal to the image pickup device 24B, the image processing section 42, and the observation image generation section 43, when detecting that the instruction to set the observation mode of the endoscope system 1 to the white light observation mode is made.

The light source control section 34 generates an LED driving signal for causing the blue LED 31A, the green LED 31B, and the red LED 31C to emit light simultaneously, and outputs the generated LED driving signal to the light emitting section 31, in the white light observation mode, in response to the control signal outputted from the control section 45. Subsequently, in response to the operation of the light source control section 34 like this, in the white light observation mode, a white light including the B light, the G light, and the R light is emitted from the light source apparatus 3 (light emitting section 31) as an illumination light, an object is irradiated with the illumination light, an image pickup signal generated by picking up an image of a return light (reflection light) of the illumination light is outputted to the signal processing section 41 from the image pickup device 24B, and image data generated based on the image pickup signal is outputted from the signal processing section 41 to the color separation processing section 42A.

The color separation processing section 42A performs color separation processing for generating B spectral image data corresponding to a blue component included in the image data, G spectral image data corresponding to a green component included in the image data, and R spectral image data corresponding to a red component included in the image data respectively by using the image data outputted from the signal processing section 41 at a time of the white light observation mode, in response to the control signal outputted from the control section 45. The color separation processing section 42A outputs to the matrix processing section 42B the B spectral image data, the G spectral image data, and the R spectral image data that are obtained as a processing result of the aforementioned color separation processing.

The matrix processing section 42B performs matrix processing for generating B component image data corresponding to the blue component by using the B spectral image data outputted from the color separation processing section 42A, generating G component image data corresponding to the green component by using the G spectral image data outputted from the color separation processing section 42A, and generating R component image data corresponding to the red component by using the R spectral image data outputted from the color separation processing section 42A, in the white light observation mode, in response to the control signal outputted from the control section 45. The matrix processing section 42B outputs to the observation image generation section 43 the B component image data, the G component image data, and the R component image data that are obtained as a processing result of the aforementioned matrix processing.

The observation image generation section 43 generates a white light observation image by allocating the B component image data outputted from the matrix processing section 42B to the B channel of the display apparatus 5, allocating the G component image data outputted from the matrix processing section 42B to the G channel of the display apparatus 5, and allocating the R component image data outputted from the matrix processing section 42B to the R channel of the display apparatus 5, in the white light observation mode, in response to the control signal outputted from the control section 45. The observation image generation section 43 outputs the white light observation image that is generated as described above to the display apparatus 5.

Figure 3:
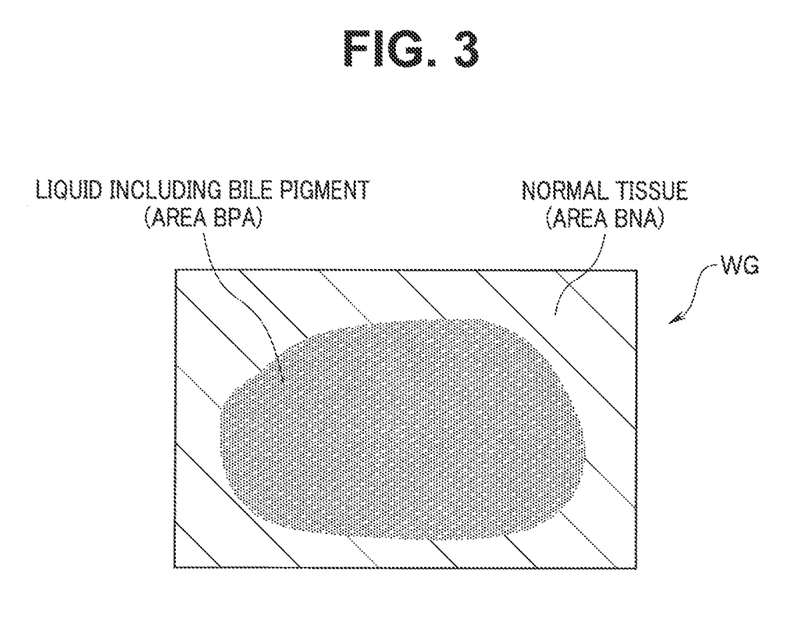
FIG. 3 is a schematic view illustrating an example of an observation image that is displayed when an observation mode of the endoscope system according to the embodiment is set to a white light observation mode.

The user inserts the insertion portion 21 into an inside of a subject, and disposes the distal end portion 23 of the insertion portion 21 in a vicinity of a desired object in the subject, while confirming the white light observation image displayed on the display apparatus 5. Thereafter, the user makes an instruction to set the observation mode of the endoscope system 1 to the special light observation mode by operating the observation mode change-over switch of the input I/F 44, in a situation where a white light observation image WG as schematically illustrated in FIG. 3 is displayed on the display apparatus 5, for example, with implementation of treatment to the desired object, and the like. Note that the white light observation image WG in FIG. 3 is assumed to show an example of a situation where it is possible to determine that lesion tissue having a mucous structure different from a mucous structure of normal tissue does not exist in an area BNA corresponding to an area that is not covered with a liquid including a bile pigment such as bile, urine, and a residue solution, of a surface of the object the image of which is picked up by the endoscope 2 (image pickup device 24B), and it is impossible to determine whether or not tissue other than normal tissue exists in an area BPA corresponding to an area that is covered with the liquid. FIG. 3 is a schematic view illustrating an example of an observation image that is displayed when the observation mode of the endoscope system according to the embodiment is set to the white light observation mode.

The control section 45 generates a control signal for causing the G light and the R light to be simultaneously emitted from the light source apparatus 3 and outputs the control signal to the light source control section 34, when detecting that an instruction to set the observation mode of the endoscope system 1 to the special light observation mode is made. The control section 45 generates a control signal for causing an operation corresponding to the special light observation mode to be performed, and outputs the control signal to the image pickup device 24B, the image processing section 42 and the observation image generation section 43, when detecting that the instruction to set the observation mode of the endoscope system 1 to the special light observation mode is made.

The light source control section 34 generates an LED driving signal for causing the green LED 31B and the red LED 31C to emit light simultaneously while turning off the blue LED 31A, and outputs the generated LED driving signal to the light emitting section 31, in the special light observation mode, in response to the control signal outputted from the control section 45. Subsequently, in response to the operation of the light source control section 34 like this, in the special light observation mode, a mixture light including the G light and the R light is emitted from the light source apparatus 3 (light emitting section 31) as an illumination light, the object is irradiated with the illumination light, an image pickup signal generated by picking up an image of a return light (reflection light) of the illumination light is outputted from the image pickup device 24B to the signal processing section 41, and image data generated based on the image pickup signal is outputted from the signal processing section 41 to the color separation processing section 42A.

The color separation processing section 42A performs color separation processing for generating G spectral image data corresponding to a green component included in the image data, and R spectral image data corresponding to a red component included in the image data respectively by using the image data outputted from the signal processing section 41 at a time of the special observation mode, in response to the control signal outputted from the control section 45. The color separation processing section 42A outputs to the matrix processing section 42B the G spectral image data and the R spectral image data that are obtained as a processing result of the aforementioned color separation processing.

The matrix processing section 42B performs such matrix processing as to generate B component image data and G component image data by applying the G spectral image data outputted from the color separation processing section 42A to equation (1) as follows, and generate R component image data by applying the R spectral image data outputted from the color separation processing section 42A to equation (1) as follows, for example, in the special light observation mode, in response to the control signal outputted from the control section 45. The matrix processing section 42B outputs to the observation image generation section 43 the B component image data, the G component image data, and the R component image data that are obtained as a processing result of the aforementioned matrix processing.

[Expression. 1]

$$\begin{pmatrix} B_{out} \\ G_{out} \\ R_{out} \end{pmatrix} = \begin{pmatrix} 1 & 0 \\ 1 & 0 \\ 0 & 1 \end{pmatrix} \begin{pmatrix} G_{in} \\ R_{in} \end{pmatrix} \quad (1)$$

Note that in a right side of equation (1) described above, Gin represents a luminance value of one pixel included in the G spectral image data, and Rin represents a luminance value of the one pixel included in the R spectral image data. In a left side of equation (1) described above, Bout represents a luminance value of one pixel included in the B component image data, Gout represents a luminance value of the one pixel included in the G component image data, and Rout represents a luminance value of the one pixel included in the R component image data.

The observation image generation section 43 generates a special light observation image by allocating the B component image data outputted from the matrix processing section 42B to the B channel of the display apparatus 5, allocating the G component image data outputted from the matrix processing section 42B to the G channel of the display apparatus 5, and allocating the R component image data outputted from the matrix processing section 42B to the R channel of the display apparatus 5 in the special light observation mode, in response to the control signal outputted from the control section 45. The observation image generation section 43 outputs the special light observation image that is generated as described above to the display apparatus 5.

In other words, according to the operation described above, the image processing section 42 generates the R component image data corresponding to the R light having the center wavelength in the vicinity of 630 nm, and the G component image data corresponding to the G light having the center wavelength in the vicinity of 540 nm respectively, based on the image data generated by the signal processing section 41 in response to the image pickup signal outputted from the image pickup device 24B, in the special light observation mode. According to the operation described above, the image processing section 42 generates the B component image data and the G component image data by using the G spectral image data generated based on the image data outputted from the signal processing section 41, and generates the R component image data by using the R spectral image data generated based on the image data, in the special light observation mode.

Figure 4:
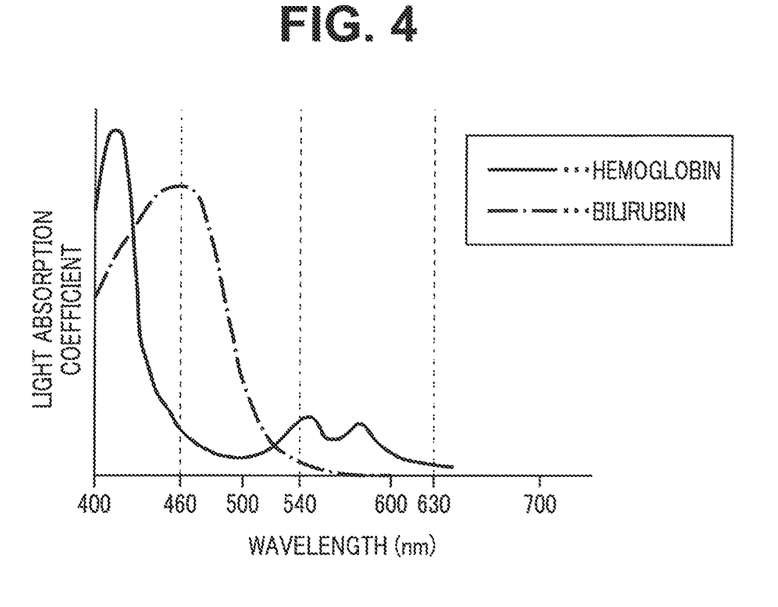
FIG. 4 is a diagram illustrating light absorption characteristics of bilirubin and hemoglobin.
Figure 5:
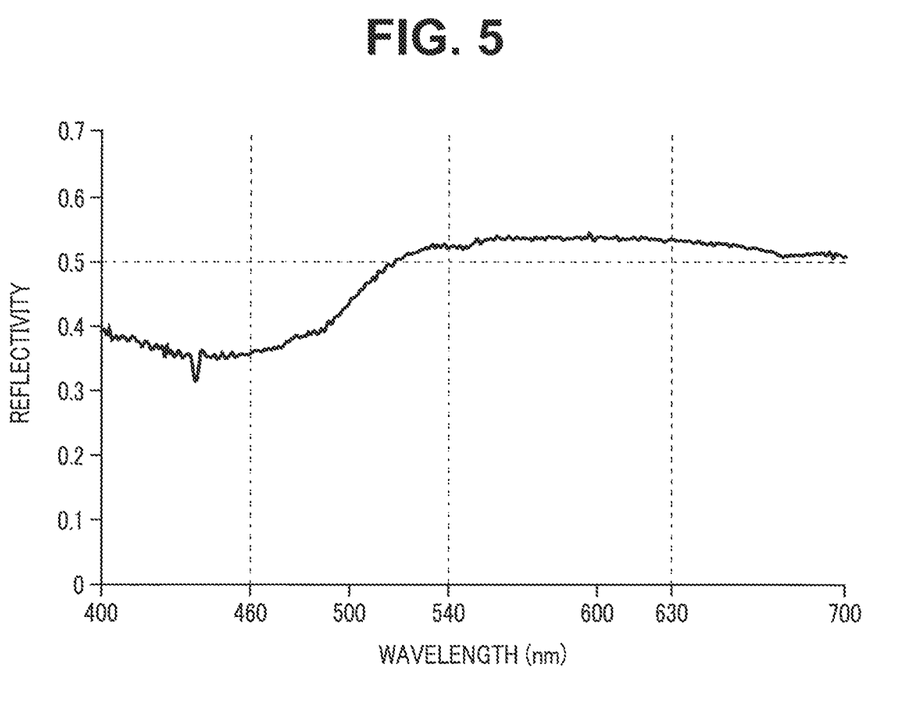
FIG. 5 is a diagram illustrating a measurement result that is obtained by actually measuring a spectral reflectivity in a mucous membrane covered with a residue solution.

Here, the R light included in the illumination light irradiated to the object in the special light observation mode has the center wavelength within a wavelength range where the light absorption coefficient in the light absorption characteristics of bilirubin corresponding to a main component of a bile pigment declines (see FIG. 4), and a scattering coefficient in scattering characteristics of living tissue declines, and therefore can substantially pass through a liquid including the bile pigment and existing in the area BPA and reach deeper than the surface of the object. According to an experimental result of the applicant, it is confirmed that a reflectivity of the R light in a mucous membrane covered with the residue solution is 50% or more as illustrated in FIG. 5. In other words, in the special light observation mode, by irradiating the object with the illumination light including the R light that is highly permeable to the liquid including a bile pigment and is difficult to scatter in living tissue, a return light (reflection light) that includes information on living tissue deeper than the surface of the object in the area BPA can be generated. FIG. 4 is a diagram illustrating light absorption characteristics of hemoglobin and bilirubin. FIG. 5 is a diagram illustrating a measurement result obtained by actually measuring a spectral reflectivity in the mucous membrane covered with the residue solution.

The G light included in the illumination light irradiated to the object in the special light observation mode has the center wavelength within a wavelength range in which the light absorption coefficient in the light absorption characteristic of bilirubin declines (see FIG. 4), the light absorption coefficient to hemoglobin is higher than the light absorption coefficient of the R light (see FIG. 4), and the scattering coefficient in the scattering characteristics of the living tissue is higher than the scattering coefficient of the R light. According to the experimental result of the applicant, it is confirmed that the reflectivity of the G light in the mucous membrane covered with the residue solution including a bile pigment is 50% or more, as illustrated in FIG. 5. In other words, in the special light observation mode, by irradiating the object with the illumination light including the G light that is highly permeable to the liquid including a bile pigment, is more easily scattered in the living tissue as compared with the R light, and is more easily absorbed by hemoglobin as compared with the R light, a return light (reflection light) that includes information relating to a mucous structure of a surface layer of the object in the area BPA and the area BNA can be generated. According to the operation of the respective sections as described above, in the special light observation mode, the object is irradiated with the illumination light including the G light to acquire the G spectral image data, and the luminance value of the acquired G spectral image data is used as two color components (the blue component and the green component) of the three color components included in the special light observation image.

Figure 6:
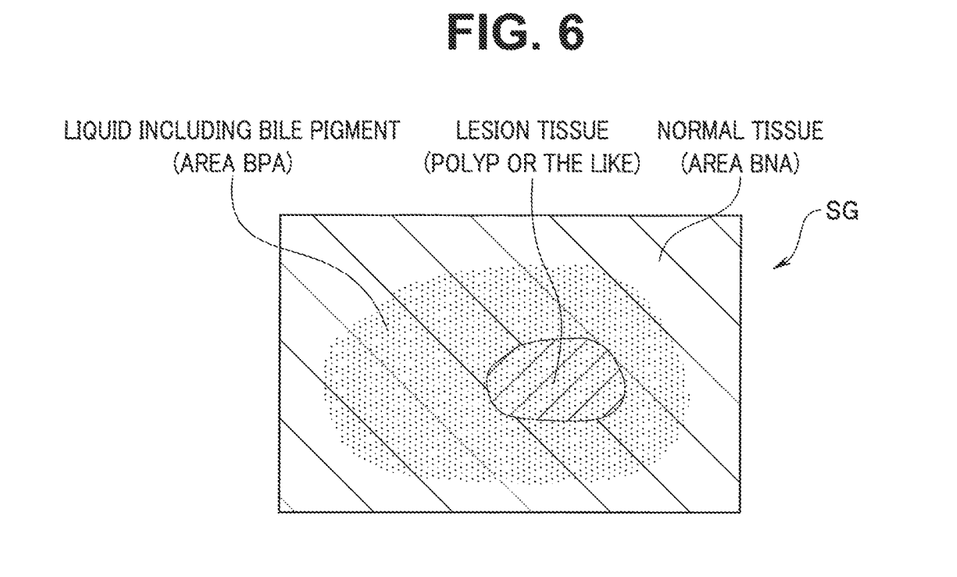
FIG. 6 is a schematic view illustrating an example of an observation image that is displayed when the observation mode of the endoscope system according to the embodiment is set to a special light observation mode.

Consequently, according to the present embodiment, when the observation mode of the endoscope system 1 is set to the special light observation mode in the situation where the white light observation image WG in FIG. 3 is displayed on the display apparatus 5, the display apparatus 5 can be caused to display a special light observation image SG in which existence of lesion tissue (polyp or the like) in the area BPA is visually recognizable, as schematically illustrated in FIG. 6. FIG. 6 is a schematic view illustrating an example of an observation image that is displayed when the observation mode of the endoscope system according to the embodiment is set to the special light observation mode.

As described above, according to the present embodiment, in the special light observation mode, it is possible to display the special light observation image having visibility that makes it possible to determine whether or not lesion tissue exists in the area covered with the liquid including a bile pigment, of the surface of the object. Therefore, according to the present embodiment, it is possible to reduce a burden on a surgeon who performs an operation in a state where at least a part of the surface of the object is covered with the liquid including a bile pigment.

Note that according to examination of the applicant, there is obtained a knowledge that a lower limit of a wavelength range in which the light absorption coefficient in the light absorption characteristics of bilirubin declines and the scattering coefficient in the living tissue declines exists in a vicinity of 615 nm. Therefore, in the present embodiment, the red LED 31C that emits the R light having a center wavelength of 615 nm or more can be provided in the light source apparatus 3. Alternatively, in the present embodiment, near infrared LD (laser diode) that emits near infrared light having a center wavelength of 800 nm or less, for example, may be provided in the light source apparatus 3.

According to the present embodiment, the matrix processing section 42B may perform such matrix processing as to generate the B component image data by using the G spectral image data outputted from the color separation processing section 42A, and generate the G component image data and the R component image data by using the R spectral image data outputted from the color separation processing section 42A in the special light observation mode by changing values of the respective components included in a 3×2 matrix on a right side of equation (1) described above to values of the respective components in equation (2) as follows, for example.

[Expression. 2]

$$\begin{pmatrix} B_{out} \\ G_{out} \\ R_{out} \end{pmatrix} = \begin{pmatrix} 1 & 0 \\ 0 & 1 \\ 0 & 1 \end{pmatrix} \begin{pmatrix} G_{in} \\ R_{in} \end{pmatrix} \quad (2)$$

In other words, in the present embodiment, the image processing section 42 can be configured to generate two color components of the three color components of the blue component, the green component and the red component that are included in the special light observation image by using the G spectral image data generated based on the image data outputted from the signal processing section 41, and to generate the one remaining color component of the three color components included in the special light observation image by using the R spectral image data generated based on the image data.

According to the present embodiment, the special light observation image that is displayed on the display apparatus 5 in the special light observation mode may be made selectable from either an image obtained through the matrix processing using equation (1) described above, and an image obtained through the matrix processing using equation (2) described above. According to the configuration like this, for example, in the special light observation mode, it is possible to perform diagnosis of lesion tissue such as polyp existing in the area BPA based on the image displayed on the display apparatus 5 through the matrix processing using equation (1) described above, and it is possible to perform treatment such as excision while avoiding tissue other than the mucous membrane existing in the area BPA, based on the image displayed on the display apparatus 5 through the matrix processing using equation (2) described above.

According to the present embodiment, for example, in the image processing section 42, 9-axis color correction processing may be performed. The 9-axis color correction processing is processing that converts the B component image data, the G component image data, and the R component image data that are outputted from the matrix processing section 42B in the special light observation mode into points on a predetermined color space that is defined by nine reference axes corresponding to respective predetermined nine hues (magenta, blue, blue cyan, cyan, green, yellow, red yellow, red, and red magenta) and corrects these data. Note that in such a case, the B component image data, the G component image data, and the R component image data that are obtained as a processing result of the aforementioned 9-axis color correction processing can be outputted to the observation image generation section 43.

According to the present embodiment, for example, in the image processing section 42, structure enhancement processing may be applied to the R component image data outputted from the matrix processing section 42B in the special light observation mode. The structure enhancement processing is processing that applies a spatial filter such as edge enhancement. In such a case, for example, in the observation image generation section 43, such an operation can be performed so as to allocate the B component image data outputted from the matrix processing section 42B to the B channel of the display apparatus 5, allocate the G component image data outputted from the matrix processing section 42B to the G channel of the display apparatus 5, and allocate the R component image data obtained as a processing result of the aforementioned structure enhancement processing to the R channel of the display apparatus 5.

According to the present embodiment, instead of the image pickup device 24B, for example, a dichroic prism and three image pickup devices may be provided in the image pickup section 24. The dichroic prism separates the light emitted through the objective optical system 24A into lights in three wavelength bands that are a light in a blue region, a light in a green region, and a light in a red region to a near infrared region and emits the lights. The three image pickup devices are to pick up images of the lights in the three wavelength bands that are emitted through the dichroic prism.

According to the present embodiment, for example, the image pickup device 24B may be configured by a monochrome image sensor. Note that in such a case, for example, in the white light observation mode, a control signal for causing the B light, the G light and the R light to be emitted in time division (sequentially) from the light source apparatus 3 can be outputted from the control section 45 to the light source control section 34. In the case as described above, for example, in the special light observation mode, a control signal for causing the B light and the R light to be emitted in time division (alternately) from the light source apparatus 3 can be outputted from the control section 45 to the light source control section 34.

According to the present embodiment, for example, in the special light observation mode, the object may be irradiated with a white light in a wider band than a light obtained by mixing the B light, the G light, and the R light as the illumination light. Note that in such a case, a return light from the object can be split into the B light, the G light, and the R light in the image pickup device 24B.

According to the present embodiment, for example, in the special light observation mode, spectral estimation processing may be performed as processing of the image processing section 42. The spectral estimation processing is such processing that estimates R spectral image data and acquires the R spectral image data by applying a predetermined spectral estimation matrix to the G image data outputted from the signal processing section 41 when the object is individually irradiated with the G light. Note that in such a case, the color separation processing section 42A is not required, and therefore, the G image data outputted from the signal processing section 41, and the R spectral image data obtained as a processing result of the aforementioned spectral estimation processing can be respectively outputted to the matrix processing section 42B.

According to the present embodiment, for example, in the special light observation mode, spectral estimation processing may be performed as processing of the image processing section 42. The spectral estimation processing is such processing that estimates G spectral image data and acquires the G spectral image data by applying a predetermined spectral estimation matrix to the R image data outputted from the signal processing section 41 when the object is individually irradiated with the R light. Note that in such a case, the color separation processing section 42A is not required, and therefore, the R image data outputted from the signal processing section 41, and the G spectral image data obtained as a processing result of the aforementioned spectral estimation processing can be respectively outputted to the matrix processing section 42B.

According to the present embodiment, for example, the light source apparatus 3 (the light emitting section 31) generates a light including the B light, the G light, and the R light as an illumination light, the color separation processing section 42A generates the B spectral image data, the G spectral image data, and the R spectral image data respectively based on the image data outputted from the signal processing section 41, the matrix processing section 42B generates the respective color components included in a white light observation image data and a special light observation image by using the B spectral image data, the G spectral image data, and the R spectral image data, and the observation image generation section 43 may cause the display apparatus 5 to display the white light observation image in combination with the special light observation image. Note that in such a case, for example, the white light observation image can be generated by using the operations of the image processing section 42 and the observation image generation section 43 in the white light observation mode, and the special light observation image can be generated by using the operations of the image processing section 42 and the observation image generation section 43 in the special light observation mode.

The present invention is not limited to the aforementioned embodiment, and it goes without saying that various modifications and applications can be made within the range without departing from the gist of the invention.

For example, in the above, the case where the present invention is an endoscope system is mainly described, but the present invention is not limited to this, but the present invention may be an image processing method of performing similar processing to the processing of the aforementioned endoscope system, a computer program for causing a computer to perform image processing, a computer-readable non-transitory recording medium that records the computer program, or the like.

What is claimed is:

1. An endoscope system comprising:
   a light source configured to generate an illumination light including:
      a first light having a center wavelength set to a vicinity of 630 nm and within a wavelength range from a red region to a near infrared region; and
      a second light having a center wavelength in a green region;
   an image sensor configured to pick up an image of an object irradiated with the illumination light and output an image pickup signal; and
   a processor comprising hardware, wherein the processor is configured to:
      generate:
         a first spectral image data corresponding to only the first light; and
         a second spectral image data corresponding to the second light, based on an image generated according to the image pickup signal; and
      based on the illumination light and the first spectral image data and the second spectral image data corresponding to the illumination light, selectively generate:
         two color components of three color components that are a blue component, a green component, and a red component included in a special light observation image that is displayed on a display at a time of observation of the object by using the second spectral image data; and
         the one remaining color component of the three color components included in the observation image by using only the first spectral image data; and
      based on the same illumination light, generate the white light observation image.

2. The endoscope system according to claim 1, wherein the processor is configured to cause the display to display the white light observation image in combination with the special light observation image, at the time of observation of the object.

3. The endoscope system according to claim 1, wherein the light source is configured to generate the illumination light including the second light with the center wavelength set to a vicinity of 540 nm.

4. The endoscope system according to claim 1, wherein the processor is configured to, based on the illumination light and the first spectral image data and the second spectral image data corresponding to the illumination light, selectively generate:
   the blue component and the green component of the three color components included in the special light observation image by using the second spectral image data; and
   the red component, as the one remaining color component of the three color components, included in the special light observation image by using the first spectral image data.

5. The endoscope system according to claim 4, wherein the processor is configured to apply structure enhancement processing to the red component generated by using the first spectral image data.

6. An image processing method comprising:
   causing a light source to generate an illumination light including:
      a first light having a center wavelength set to a vicinity of 630 nm and within a wavelength range from a red region to a near infrared region; and
      a second light having a center wavelength in a green region;
   causing an image sensor to pick up an image of an object irradiated with the illumination light and to output an image pickup signal;
   generating:
      a first spectral image data corresponding to only the first light; and
      a second spectral image data corresponding to the second light, based on an image generated according to the image pickup signal; and
   based on the illumination light and the first spectral image data and the second spectral image data corresponding to the illumination light, selectively generating:
      two color components of three color components that are a blue component, a green component, and a red component included in a special light observation image that is displayed on a display at a time of observation of the object by using the second spectral image data; and the one remaining color component of the three color components included in the special light observation image by using only the first spectral image data; and based on the same illumination light, generating the white light observation image.

7. The image processing method according to claim 6, further comprising:

causing the display to display the white light observation image in combination with the special light observation image, at the time of observation of the object.

8. The image processing method according to claim 6, wherein causing the light source to generate the illumination light includes generating the second light with the center wavelength set to a vicinity of 540 nm.

9. The image processing method according to claim 6, wherein selectively generating the two color components and the one remaining color component comprises selectively generating:

the blue component and the green component of the three color components included in the special light observation image using the second spectral image data; and the red component, as the one remaining color component of the three color components, included in the special light observation image is generated by using the first spectral image data.

10. The image processing method according to claim 9, further comprising:

applying structure enhancement processing to the red component generated by using the first spectral image data.

11. An endoscope system comprising:

a light source configured to generate an illumination light, the light source being configured to emit a first light having a center wavelength set to a vicinity of 630 nm and within a wavelength range from a red region to a near infrared region and a second light having a center wavelength in a green region;

an image sensor configured to pick up an image of an object irradiated with the illumination light and output an image pickup signal; and a processor comprising hardware, wherein the processor is configured to:

generate:

a first spectral image data corresponding to only the first light; and a second spectral image data corresponding to the second light, based on an image generated according to the image pickup signal; and based on the illumination light and the first spectral image data and the second spectral image data corresponding to the illumination light, selectively generate;

two color components of three color components that are a blue component, a green component, and a red component included in a special light observation image that is displayed on a display at a time of observation of the object by using the second spectral image data; and the one remaining color component of the three color components included in the observation image by using only the first spectral image data; and based on the same illumination light, generate the white light observation image.

12. The endoscope system according to claim 11, wherein the processor is configured to cause the display to display the white light observation image in combination with the special light observation image, at the time of observation of the object.

13. The endoscope system according to claim 11, wherein the light source is configured to generate the illumination light including the second light with the center wavelength set to a vicinity of 540 nm.

14. The endoscope system according to claim 11, wherein the processor is configured to, based on the illumination light and the first spectral image data and the second spectral image data corresponding to the illumination light, selectively generate:

the blue component and the green component of the three color components included in the special light observation image by using the second spectral image data; and the red component, as the one remaining color component of the three color components, included in the special light observation image by using the first spectral image data.

15. The endoscope system according to claim 14, wherein the processor is configured to apply structure enhancement processing to the red component generated by using the first spectral image data.

* * * * *